US012582596B2

(12) United States Patent
Lobmueller et al.

(10) Patent No.: US 12,582,596 B2
(45) Date of Patent: Mar. 24, 2026

(54) SOLID COMPOSITION FOR KERATIN FIBERS

(71) Applicant: KAO CORPORATION, Tokyo (JP)

(72) Inventors: Petra Lobmueller, Darmstadt (DE); Andreas Picker, Darmstadt (DE); Anja Aechtner, Darmstadt (DE)

(73) Assignee: KAO CORPORATION, Tokyo (JP)

( * ) Notice: Subject to any disclaimer, the term of this patent is extended or adjusted under 35 U.S.C. 154(b) by 235 days.

(21) Appl. No.: 17/643,055

(22) Filed: Dec. 7, 2021

(65) Prior Publication Data

US 2022/0192969 A1 Jun. 23, 2022

(30) Foreign Application Priority Data

Dec. 17, 2020 (EP) .................................... 20214969

(51) Int. Cl.

*A61K 8/92* (2006.01)
*A61K 8/02* (2006.01)
*A61K 8/33* (2006.01)
*A61K 8/34* (2006.01)
*A61K 8/37* (2006.01)
*A61K 8/46* (2006.01)
*A61K 8/73* (2006.01)
*A61Q 5/12* (2006.01)

(52) U.S. Cl.

CPC ............ *A61K 8/922* (2013.01); *A61K 8/0216* (2013.01); *A61K 8/33* (2013.01); *A61K 8/342* (2013.01); *A61K 8/37* (2013.01); *A61K 8/463* (2013.01); *A61K 8/731* (2013.01); *A61Q 5/12* (2013.01)

(58) Field of Classification Search

CPC .. A61K 2800/31; A61K 8/922; A61K 8/0216; A61K 8/33; A61K 8/342; A61K 8/37; A61K 8/463; A61K 8/731; A61K 8/19; A61K 8/416; A61K 8/92; A61K 8/0241; A61Q 5/12

See application file for complete search history.

(56) References Cited

U.S. PATENT DOCUMENTS

| | | | | |
|---|---|---|---|---|
| 6,607,718 B1 * | 8/2003 | Okuno | A61K 8/365 | 424/70.13 |
| 2003/0008790 A1 * | 1/2003 | Carew | A61Q 5/12 | 510/141 |
| 2005/0008604 A1 * | 1/2005 | Schultz | A61Q 19/00 | 424/59 |
| 2006/0110415 A1 * | 5/2006 | Gupta | A61K 8/0212 | 424/59 |
| 2011/0135587 A1 | 6/2011 | Kinoshita et al. | | |
| 2015/0050230 A1 * | 2/2015 | Yang | A61Q 5/002 | 424/70.11 |
| 2016/0143827 A1 | 5/2016 | Castan Barberan et al. | | |
| 2018/0333339 A1 | 11/2018 | Hamersky et al. | | |

FOREIGN PATENT DOCUMENTS

| | | | |
|---|---|---|---|
| EP | 2316414 A1 * | 5/2011 | A61K 8/342 |
| EP | 2 818 155 A1 | 12/2014 | |
| EP | 3 597 172 A1 | 1/2020 | |
| WO | WO 2013/175221 A2 | 11/2013 | |
| WO | WO-2018213003 A1 * | 11/2018 | A61K 8/0216 |
| WO | WO 2020/133212 A1 | 7/2020 | |
| WO | WO 2021/004674 A1 | 1/2021 | |

OTHER PUBLICATIONS

European Search Report issued Jun. 10, 2021 in European Application 2021 4969.6 filed Dec. 17, 2020, 2 pages.
Database GNPD Mintel "Conditioner Reinvented The Restoring One", Dec. 18, 2019, 8 pages.

* cited by examiner

*Primary Examiner* — Marianne C Seidel
*Assistant Examiner* — Amanda Michelle Petritsch
(74) *Attorney, Agent, or Firm* — Oblon, McClelland, Maier & Neustadt, L.L.P.

(57) ABSTRACT

The present invention is directed to a solid cosmetic composition for keratin fibers, preferably human keratin fibers, more preferably human hair, comprising: one or more non-silicone lipophilic compound(s) having a melting point above 25° C. under atmospheric pressure, one or more pulverulent excipient(s), one or more cationic and/or cationizable compound(s), wherein the concentration of pulverulent excipients is 1% by weight or more, calculated to the total weight of the composition, and wherein the total concentration of water is less than 10% by weight, preferably less than 5% by weight, more preferably less than 1% by weight, still more preferably less than 0.5% by weight, calculated to the total weight of the composition.

13 Claims, No Drawings

SOLID COMPOSITION FOR KERATIN FIBERS

CROSS REFERENCES TO RELATED APPLICATIONS

This application claims priority to European Patent Application No. 20214969.6, filed on Dec. 17, 2020, which is incorporated herein by reference in it entirety.

FIELD OF THE INVENTION

The present invention is directed to a solid composition for keratin fibers, preferably human keratin fibers, more preferably human hair. In addition, a method for conditioning keratin fibers is disclosed.

BACKGROUND OF THE INVENTION

Solid personal care formulations are getting more and more popular as they support the image of sustainable, water-free and natural product formats. While solid shampoo bars are omnipresent in the hair care market, solid conditioner bars are rare. One reason might be the hurdle to formulate a temperature stable product, which is still convenient to use. Conditioner bars are normally based on fatty alcohols or waxes with high melting point to guarantee stability at temperatures up to 40 degrees. However, the easiness of product uptake is highly reduced upon the usage of high melting raw materials. Thus, product stability and easiness of product uptake/abrasion are contradictory parameters.

WO2013/175221 disclose solid cosmetic composition comprising fatty alcohol, a bulking agent, and anionic surfactant. The purpose is for cleansing skin and hair.

SUMMARY OF THE INVENTION

The first object of the present invention is a solid cosmetic composition for keratin fibers, preferably human keratin fibers, more preferably human hair, comprising:

a) one or more non-silicone lipophilic compound(s) having a melting point above 25° C. under atmospheric pressure, b) one or more pulverulent excipient(s), c) one or more cationic and/or cationizable compound(s), wherein the concentration of compound b) is 1% by weight or more, calculated to the total weight of the composition, and wherein the total concentration of water is less than 10% by weight, preferably less than 5% by weight, more preferably less than 1% by weight, still more preferably less than 0.5% by weight, calculated to the total weight of the composition, and wherein one or more compound(s) according to group b) is/are a chemically unmodified or chemically-modified cellulose, nylon powder, sawdust, perlite, natural or chemically-modified starch.

The second object of the present invention is a method for conditioning keratin fibers, preferably human keratin fibers, more preferably human hair, comprising the steps of:

i) optionally wetting the user's hand(s), ii) rubbing the solid composition as defined above in the palm of the hand, preferably the wet palm of the hand, and/or under running tap water, for a time period in the range of 5 s to 120 s and dissolving, removing solid parts and/or melting parts from it, iii) putting the solid composition aside and touching the keratin fibers with the hand(s) having applied the composition, iv) massaging the composition into the keratin fibers and optionally rinsing-off the product, v) optionally blow-drying and styling the keratin fibers.

DETAILED DESCRIPTION OF THE INVENTION

The inventors of the present invention surprisingly found that solid compositions according to claim 1 result in an easy product uptake/abrasion while the product stability at higher temperatures is improved at the same time. These two parameters are normally contradictory to each other. The present invention delivers a solution to this contradiction.

Composition

The present invention is directed to a solid cosmetic composition for keratin fibers, preferably human keratin fibers, more preferably human hair, comprising:

a) one or more non-silicone lipophilic compound(s) having a melting point above 25° C. under atmospheric pressure, b) one or more pulverulent excipient(s), c) one or more cationic and/or cationizable compound(s), wherein the concentration of compound b) is 1% by weight or more, calculated to the total weight of the composition, and wherein the total concentration of water is less than 10% by weight, preferably less than 5% by weight, more preferably less than 1% by weight, still more preferably less than 0.5% by weight, calculated to the total weight of the composition, and wherein one or more compound(s) according to group b) is/are a chemically unmodified or chemically-modified cellulose, nylon powder, sawdust, perlite, natural or chemically-modified starch.

It is also further preferred from the viewpoint of stability that the composition is an anhydrous composition.

The term 'anhydrous' within the meaning of the present invention denotes a composition without added water. Thus, the presence of crystal water or adherent water is not excluded.

The composition of the present invention is solid. The term 'solid' within the meaning of the present invention refers to the aggregate state at room temperature (25° C.) and atmospheric pressure.

It is further preferred from the product convenience that the composition of the present invention is in the form of a conditioning bar. Such a bar is a solidified melt of the ingredients according to claim 1.

Compound(s) According to a)

The present invention comprises one or more non-silicone lipophilic compound(s) having a melting point above 20° C. under atmospheric pressure as compound(s) according to a).

The term 'non-silicone' denotes a compound that is free of silicon atoms.

The term 'lipophilic' denotes a compound, which does not fully mix at a concentration of 5% by weight with water in a molten and/or liquid state under atmospheric pressure.

It is preferred from the viewpoint of biodegradability that one or more compound(s) according to group a) is/are $C_{12}$ to $C_{22}$ fatty alcohols, $C_{12}$ to $C_{22}$ fatty acid monoesters of $C_6$ to $C_{22}$ alcohols, $C_{12}$ to $C_{22}$ fatty acids, cocoa butter, shea butter, astrocaryum murumuru seed butter, coconut seed butter, palm butter, strawberry seed butter, avocado butter, mango butter, cocoa butter, sesame butter, jojoba butter, hydrogenated vegetable oil, and/or their mixtures.

Suitable $C_{12}$ to $C_{22}$ fatty alcohols have a saturated alkyl chain. Suitable examples are lauryl alcohol, cetyl alcohol, stearyl alcohol, cetearyl alcohol, myristyl alcohol, pentadecyl alcohol, behenyl alcohol, and/or their mixtures.

Suitable $C_{12}$ to $C_{22}$ fatty acid monoesters of $C_6$ to $C_{22}$ alcohols are, for example, myristyl myristate, myristyl palmitate, cetyl palmitate, palmityl palmitate, and/or their mixtures.

Suitable $C_{12}$ to $C_{22}$ fatty acids are, for example, lauric acid or stearic acid.

It is preferred from the viewpoint of conditioning performance that the total concentration of compound(s) according to group a) is 30% by weight or more, preferably 40% by weight or more, further more preferably 50% by weight or more, still further more preferably 60% by weight or more, calculated to the total weight of the composition.

It is preferred from the viewpoint of low weight down effect that the total concentration of compound(s) according to group a) is 90% by weight or less, preferably 85% by weight or less, further more preferably 80% by weight or less, still further more preferably 75% by weight or less, calculated to the total weight of the composition.

For attaining the above-mentioned effects, it is preferred that the total concentration of compound(s) according to group a) is in the range of 30% to 90% by weight, preferably 40% to 85% by weight, further more preferably 50% to 80% by weight, still further more preferably 60% to 75% by weight, calculated to the total weight of the composition.

Compound(s) According to Group b)

The composition of the present invention comprises one or more pulverulent excipients having a concentration of 1% by weight or more, calculated to the total weight of the composition.

The pulverulent excipients are chemically unmodified or chemically-modified cellulose(s), nylon powder, sawdust, perlite, natural or chemically-modified starch(es) as pulverulent excipient(s).

It is preferred from the viewpoint of abrasion that the total concentration of chemically unmodified or chemically-modified cellulose(s), nylon powder, sawdust, perlite, natural or chemically-modified starch(es) as pulverulent excipient(s) is 1% by weight or more, calculated to the total weight of the composition.

The term chemically unmodified cellulose within the meaning of the present invention is a cellulose, which has not undergone partial-synthetic modification at its hydroxy groups, i.e., in chemically unmodified cellulose the hydroxy groups are free.

The term chemically-modified cellulose within the meaning of the present invention is a cellulose which has undergone partial-synthetic modification at its hydroxy groups, i.e., in chemically modified cellulose the hydroxy groups have partially or completely reacted with chemical moieties, for example, with moieties having alkyl chain in the range of $C_1$ to $C_{12}$.

The term natural starches within the meaning of the present invention is a starch that has been extracted from plants and which has not undergone partial-synthetic modification at its hydroxy groups.

The term chemically-modified starch within the meaning of the present invention is a starch that has been extracted from plants which has undergone partial-synthetic modification at its hydroxy groups, i.e. in chemically-modified starch the hydroxy groups have partially or completely reacted with chemical moieties, for example, with moieties having alkyl chain in the range of $C_1$ to $C_{12}$.

Suitable compounds are chemically unmodified cellulose, cetyl hydroxyethylcellulose, hydroxyethylcellulose, hydroxypropylcellulose, methylcellulose, oat starch, corn starch, rice starch, wheat starch, tapioca starch, modified corn starch, and/or their mixtures.

It is preferred from the viewpoint of abrasive properties that the total concentration of compound(s) according to group b), preferably the total concentration of chemically unmodified or chemically-modified cellulose, nylon powder, sawdust, perlite, natural or chemically-modified starch, is 2% by weight or more, more preferably 3% by weight or more, further more preferably 3.5% by weight or more, calculated to the total weight of the composition.

It is preferred from the viewpoint of melting properties that the total concentration of compound(s) according to group b), preferably the total concentration of chemically unmodified or chemically-modified cellulose, nylon powder, sawdust, perlite, natural or chemically-modified starch, is 20% by weight or less, more preferably 15% by weight or less, further more preferably 12% by weight or less, calculated to the total weight of the composition.

For attaining the above-mentioned effects, it is preferred that the total concentration of compound(s) according to group b), preferably the total concentration of chemically unmodified or chemically-modified cellulose, nylon powder, sawdust, perlite, natural or chemically-modified starch, is in the range of 2% to 20% by weight, more preferably in the range of 3% to 15% by weight, further more preferably in the range of 3.5% to 12% by weight, calculated to the total weight of the composition.

It is preferred from the viewpoint of abrasion and biodegradability that one or more compound(s) according to group b) is chemically unmodified cellulose and the total concentration of chemically unmodified cellulose is in the range of 2% to 20% by weight, preferably in the range of 3% to 15% by weight, more preferably in the range of 3.5% to 12% by weight, calculated to the total weight of the composition.

Compound(s) According to Group c)

The composition of the present invention comprises one or more cationic and/or cationizable compound(s) as compound(s) according to group c).

The term 'cationizable' denotes compounds, which are non-ionic under certain pH conditions, but may carry a cationic charge, especially under acidic conditions. Suitable cationizable groups are, for example, primary, secondary or tertiary amines.

It is preferred from the viewpoint of biodegradability that one or more compound(s) according to group c) is/are non-silicone compound(s).

In principle, any cationic and/or cationizable compound is suitable for the present invention. For example, one or more compound(s) according to group c) may be a cationic polymer, preferably a cationic polymer known under the INCI names Polyquaternium.

However, from the viewpoint of conditioning performance it is preferred that one or more compound(s) according to group c) is a quaternary ammonium salt surfactant, an alkylamine surfactant, an alkylamidoalkylamine surfactant, and/or their mixtures, and/or their salt(s).

Suitable compound(s) according to c) is/are cetrimonium chloride, steartrimonium chloride, behentrimonium chloride, soytrimonium chloride, palmitamidopropyltrimonium chloride, stearamidopropyldimethylamine, behenamidopropyldimethylamine methosulfate, bis-(isostearoyl/oleoyl isopropyl) dimonium methosulfate, dicetyldimonium chloride, distearoylethyl dimonium chloride, tricetylmonium chloride, and/or their mixtures.

It is preferred from the viewpoint of biodegradability that the total concentration of one or more compound(s) according to group c) is 0.5% by weight or more, preferably 1% by weight or more, further more preferably 2% by weight or more, calculated to the total weight of the composition.

It is preferred from the viewpoint of conditioning performance that the total concentration of one or more compound(s) according to group c) is 10% by weight or less, more preferably 8% by weight or less, further more preferably 6% by weight or less, calculated to the total weight of the composition.

For attaining the above-mentioned effects, it is preferred that the total concentration of compound(s) according to group c) is in the range of 0.5% to 10% by weight, preferably in the range of 1% to 8% by weight, more preferably in the range of 2% to 6% by weight, calculated to the total weight of the composition.

Compound(s) According to Group d)

Optionally, the composition of the present invention may comprise one or more natural oil being liquid at 25° C. and atmospheric pressure as compound(s) according to d), from the viewpoint of increasing natural feel of keratin fibers.

Suitable compound(s) according to group d) is/are sweet almond oil, grapeseed oil, sunflower oil, rapeseed oil, olive oil, wheat kernel oil, oat kernel oil, broccoli seed oil, *Camellia sinensis* seed oil, *Cannabis sativa* seed oil, coffee seed oil, hazelnut seed oil, walnut seed oil, castor oil, rice seed oil, and/or their mixtures.

It is preferred from the viewpoint of conditioning performance that the total concentration of compound(s) according to group d) is in the range of 3% by weight or more, preferably 5% by weight or more, further more preferably 7.5% by weight or more, calculated to the total weight of the composition.

It is preferred from the viewpoint of biodegradability that the total concentration of compound(s) according to group d) is in the range of 25% by weight or more, preferably 20% by weight or more, further more preferably 15% by weight or more, calculated to the total weight of the composition.

For attaining the above-mentioned effects it is preferred that the total concentration of compound(s) according to group d) is in the range of 3% to 25% by weight, more preferably in the range of 5% to 20% by weight, further more preferably in the range of 7.5% to 15% by weight, calculated to the total weight of the composition.

Compound(s) According to e)

Optionally, the composition of the present invention may comprise one or more non-ionic surfactant as compound(s) according to group e).

Suitable non-ionic surfactants are of N-alkylpolyhydroxyalkylamide type according to the following general formula:

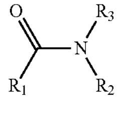

wherein $R_1$ is a linear or branched, saturated or unsaturated alkyl chain with $C_{11}$ to $C_{21}$, $R_2$ is linear or branched alkyl, or linear or branched hydroxyalkyl with $C_1$ to $C_4$, and $R_3$ is a linear or branched polyhydroxyalkyl chain with $C_3$ to $C_{12}$ and 3 to 10 hydroxyl groups.

Such compounds are disclosed in cosmetic compositions in WO96/27366 and their synthesis is disclosed in US1985424, US2016962, US2703798, and WO92/06984.

The preferred N-alkylpolyhydroxyalkylamide type surfactants have the following structure:

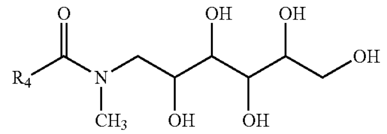

where $R_4$ has the same denotation as above for the general structure of N-alkylpolyhydroxyalkylamide type surfactants. The preferred surfactants as displayed above are known as N-methyl-N-acylglucamides.

The most preferred N-alkylpolyhydroxyalkylamide type surfactants are selected from lauroyl/myristoyl methyl glucamide, coco methyl glucamide, and capryloyl caproyl methyl glucamide.

Further suitable non-ionic surfactants are alkyl glycosides or alkyl polyglycosides according to the general structure:

$$R_5O(R_6O)_tZ_x$$

Wherein Z denotes a carbohydrate with $C_5$ to $C_6$, $R_5$ is an alkyl group with $C_8$ to $C_{18}$, $R_6$ is methyl, ethyl or propyl, t ranges from 0 to 10, and x ranges from 1 to 5. Suitable compounds according to this structure are $C_9$-$C_{11}$ alkylpolyglycoside, the structures disclosed in EP-A 70 074, and JP 2015-123019A.

The preferred compounds according to the structure of above are decyl glucoside, lauryl glucoside, and coco glucoside, and the most preferred one is coco glucoside.

Suitable examples for non-ionic surfactants are fatty alcohol ethoxylates of the following general structure $$R_7(OCH_2CH_2)_{n1}OH$$

wherein $R_7$ is straight or branched, saturated or unsaturated alkyl chain which may be synthetic or natural with a C chain length in the range of 8 to 40, preferably 9 to 30 and more preferably 9 to 24 and n1 is a number in the range of 5 to 40, preferably 9 to 30.

Non-limiting suitable examples of the fatty alcohol ethoxylates are C9-11 Pareth-6, C9-11 Pareth-8, C9-15 Pareth-8, C11-13 Pareth-9, C11-13 Pareth-10, C11-15 Pareth-5, C11-15 Pareth-7, C11-15 Pareth-9, C11-15 Pareth-12, C11-15 Pareth-15, C11-15 Pareth-20, C11-15 Pareth-30, C11-15 Pareth-40, C11-21 Pareth-10, C12-13 Pareth-5, C12-13 Pareth-6, C12-13 Pareth-7, C12-13 Pareth-9, C12-13 Pareth-10, C12-13 Pareth-15, C12-13 Pareth-23, C12-14 Pareth-5, C12-14 Pareth-7, C12-14 Pareth-9, C12-14 Pareth-11, C12-14 Pareth-12, C12-15 Pareth-5, C12-15 Pareth-7, C12-15 Pareth-9, C12-15 Pareth-10, C12-15 Pareth-11, C12-15 Pareth-12, C12-16 Pareth-5, C12-16 Pareth-7, C12-16 Pareth-9, C13-15 Pareth-21, C14-15 Pareth-7, C14-15 Pareth-8, C14-15 Pareth-11, C14-15 Pareth-12, C14-15 Pareth-13, C20-22 Pareth-30, C20-40 Pareth-10, C20-40 Pareth-24, C20-40 Pareth-40, C20-40 Pareth-95, C22-24 Pareth-33, Beheneth-5, Beheneth-10, Beheneth-15, Beheneth-20, Beheneth-25, Beheneth-30, Ceteareth-5, Ceteareth-6, Ceteareth-7, Ceteareth-10, Ceteareth-11, Ceteareth-12, Ceteareth-15, Ceteareth-20, Ceteareth-25, Ceteareth-30, Ceteareth-35, Ceteareth-40, Laureth-5, Laureth-10, Laureth-15, Laureth-20, Laureth-25, Laureth-30, Laureth-40, Myreth-5, Myreth-10, Ceteth-5, Ceteth-10, Ceteth-15, Ceteth-20, Ceteth-25, Ceteth-30, Ceteth-40, Oleth-5, Oleth-10, Oleth-15, Oleth-20, Oleth-25, Oleth-30, Oleth-40, Steareth-5, Steareth-10, Steareth-15, Steareth-20, Steareth-25, Steareth-30, Steareth-35, and Steareth-40. They may also be comprised in the compositions as a mixture of more than one surfactant.

Further suitable nonionic surfactants are polypropylene glycol ethers of fatty alcohols according to general structure $$R_8(OCH_2—CH_2—CH_2)_{n2}OH$$

wherein $R_8$ is straight or branched, saturated or unsaturated fatty alcohol which may be synthetic or natural with a C chain length in the range of 8 to 40, preferably 9 to 30 and more preferably 9 to 24 and n2 is a number in the range of 1 to 40, preferably 3 to 30.

Suitable non-limiting examples are PPG-3 Caprylyl ether, PPG-5 Caprylyl ether, PPG-10 Caprylyl ether, PPG-10 Cetyl ether, PPG-20 Cetyl ether, PPG-28 Cetyl ether, PPG-30 Cetyl ether, PPG-7 Lauryl ether, PPG-10 Lauryl ether, PPG-10 Oleyl ether, PPG-20 Oleyl ether, PPG-23 Oleyl ether, PPG-30 Oleyl ether, PPG-11 Stearyl ether and PPG-15 Stearyl ether.

Further suitable nonionic surfactants are polyethylene glycol fatty acid esters of the following general structure $$R_9C(O)(OCH_2CH_2)_{n2}OH$$

wherein $R_9$ is straight or branched, saturated or unsaturated alkyl group which may be synthetic or natural with a C chain length in the range of 7 to 39, preferably 9 to 29 and more preferably 9 to 23 and n6 is a number in the range of 5 to 40, preferably 9 to 30.

Suitable non-limiting examples are PEG-8 Behenate, PEG-8 Caprate, PEG-8 Caprylate, PEG-5 Cocoate, PEG-8 Cocoate, PEG-9 Cocoate, PEG-10 Cocoate, PEG-15 Cocoate, PEG-6 Isopalmitate, PEG-6 Isostearate, PEG-8 Isostearate, PEG-9 Isostearate, PEG-10 Isostearate, PEG-12 Isostearate, PEG-20 Isostearate, PEG-30 Isostearate, PEG-40 Isostearate, PEG-6 Laurate, PEG-8 Laurate, PEG-9 Laurate, PEG-10 Laurate, PEG-12 Laurate, PEG-14 Laurate, PEG-20 Laurate, PEG-30 Laurate, PEG-8 Myristate, PEG-20 Myristate, PEG-5 Oleate, PEG-6 Oleate, PEG-7 Oleate, PEG-8 Oleate, PEG-9 Oleate, PEG-10 Oleate, PEG-11 Oleate, PEG-12 Oleate, PEG-15 Oleate, PEG-20 Oleate, PEG-30 Oleate, PEG-32 Oleate, PEG-6 Palmitate, PEG-18 Palmitate, PEG-20 Palmitate, PEG-5 Stearate, PEG-6 Stearate, PEG-7 Stearate, PEG-8 Stearate, PEG-9 Stearate, PEG-10 Stearate, PEG-12 Stearate, PEG-14 Stearate, PEG-15 Stearate, PEG-20 Stearate, PEG-25 Stearate, PEG-30 Stearate, PEG-35 Stearate and PEG-40 Stearate.

Further suitable nonionic surfactants are polypropylene glycol fatty acid esters of the following general structure $$R_{10}C(O)(OCH_2—CH_2—CH_2)_{n3}OH$$

wherein $R_{10}$ is straight or branched, saturated or unsaturated alkyl group which may be synthetic or natural with a C chain length in the range of 7 to 39, preferably 9 to 29 and more preferably 9 to 23 and n3 is a number in the range of 1 to 40, preferably 9 to 30.

Suitable non-limiting examples are PPG-15 Isostearate, PPG-9 Laurate, PPG-26 Oleate and PPG-36 Oleate.

Further suitable nonionic surfactants are polyethylene glycol and polypropylene glycol ether of fatty alcohols of the following general structure $$R_{11}(OCH_2—CH_2—CH_2)_{n4}(OCH_2CH_2)_{n5}OH$$

wherein $R_{11}$ is straight or branched, saturated or unsaturated alkyl group which may be synthetic or natural with a C chain length in the range of 7 to 39, preferably 9 to 29 and more preferably 9 to 23 and n4 and n5 may be the same or different and are a number in the range of 1 to 40.

Further suitable nonionic surfactants are ethoxylated vegetable oils. Well-known and commonly used examples are ethoxylated castor oil such as PEG-40 hydrogenated castor oil or and PEG-60 hydrogenated castor oil.

It is preferred from the viewpoint of wettability that one or more compound(s) according to group e) is/are polypropylene glycol ethers of fatty alcohols, and/or their mixtures.

It is preferred from the viewpoint of keratin fiber wettability that the total concentration of compound(s) according to group e) is 0.5% by weight or more, more preferably 1% by weight or more, further more preferably 2% by weight or more, calculated to the total weight of the composition.

It is preferred from the viewpoint of composition stability that the total concentration of compound(s) according to group e) is 15% by weight or less, more preferably 10% by weight or less, further more preferably 8% by weight or less, calculated to the total weight of the composition.

For attaining the above-mentioned effects, it is preferred that the total concentration of compound(s) according to group e) is in the range of 0.5% to 15% by weight, preferably in the range of 1% to 10% by weight, more preferably in the range of 2% to 8% by weight, calculated to the total weight of the composition.

It is further preferred from the viewpoint of composition stability that the weight ratio of compound(s) according to group c) to compound(s) according to group e) is in the range of 0.2 to 5, preferably in the range of 0.3 to 3, more preferably in the range of 0.5 to 2.

Method for Conditioning of Keratin Fibers

The present invention is also directed to a method for conditioning keratin fibers, preferably human keratin fibers, more preferably human hair, comprising the steps of:

i) optionally wetting the user's hand(s), ii) rubbing the solid composition as defined above in the palm of the hand, preferably the wet palm of the hand, and/or under running tap water, for a time period in the range of 5 s to 120 s and dissolving, removing solid parts and/or melting parts from it, iii) putting the solid composition aside and touching the keratin fibers with the hand(s) having applied the composition, iv) massaging the composition into the keratin fibers and optionally rinsing-off the product, v) optionally blow-drying and styling the keratin fibers.

It is preferred from the viewpoint of user convenience, that the user wets the hand(s) with water, preferably warm water, prior to step ii).

It is preferred in step ii), that the solid composition according to the present inventions dissolves in the wet hand(s) of the user. From this viewpoint, it is preferred to have wetted the hand(s) prior to step ii). However, for impatient users, wetting of step i) and rubbing of step ii) may be performed simultaneously.

The massaging step of iv) may last for a time period in the range of 5 s to 120 s, preferably for a time period in the range of 10 s to 60 s.

It is preferred from the viewpoint of user convenience, that in step v) the keratin fibers are blow-dried in a temperature range from 45° C. to 110° C. and treated with a tool such as a brush or a comb.

Other features of the invention will become apparent in the course of the following descriptions of exemplary embodiments which are given for illustration of the invention and are not intended to be limiting thereof.

Examples

Methods

Melting Test

The solid compositions were placed into a closed glass box and stored at 40° C. over 14 days. Visual appearance was judged after storage.

Abrasion Test

The solid composition was wetted with warm water (38-40° C.) and weighed. This wet weight served as reference starting weight. The users hands were wetted with lukewarm water and the composition was then rubbed in the palm of the hand for 20 s. Then the residual weight of the solid composition was determined. The weight difference before and after rubbing was then reported for each rubbing step in the table above. The process was repeated for 15 times.

Statistical analysis was performed using ANOVA-testing combined with Tukey's post-hoc test to determine the p-value.

The following compositions were prepared by melting the compounds above 70° C., then pouring them into a silicone mold having the following dimensions: 50 mm length, 30 mm width, 20 mm height. Then they were allowed to cool overnight.

| | Ingredients | Inv. comp. 1 | Inv. comp. 2 [% by weight] | Comp. comp. |
|---|---|---|---|---|
| a) | Cetearyl alcohol | 42.0 | 42.0 | 42.0 |
| | Shea butter | 22.5 | 20.0 | 25.0 |
| | Myristyl myristate | 3.0 | 3.0 | 3.0 |
| | Cocoa butter | 5.0 | 5.0 | 5.0 |
| d) | Almond oil | 16.5 | 14.0 | 19.0 |
| c) | Behentrimonium methosulfate | 3.0 | 3.0 | 3.0 |
| b) | Cellulose | 5.0 | 10.0 | — |
| e) | PEG-3 caprylyl ether | 3.0 | 3.0 | 3.0 |
| Evaluation | Melting after 14 days at 40° C. | Low melting | No melting | Strong melting |

Abrasion Test Results

| Test run | Inv. comp. 1 | Inv. comp. 2 [g] | Comp. comp. |
|---|---|---|---|
| 1 | 0.22 | 0.32 | 0.12 |
| 2 | 0.25 | 0.37 | 0.17 |
| 3 | 0.24 | 0.54 | 0.11 |
| 4 | 0.27 | 0.46 | 0.09 |
| 5 | 0.30 | 0.34 | 0.13 |
| 6 | 0.25 | 0.37 | 0.10 |
| 7 | 0.18 | 0.32 | 0.10 |
| 8 | 0.24 | 0.42 | 0.08 |
| 9 | 0.26 | 0.39 | 0.12 |
| 10 | 0.25 | 0.32 | 0.11 |
| 11 | 0.17 | 0.48 | 0.10 |
| 12 | 0.24 | 0.46 | 0.12 |
| 13 | 0.24 | 0.48 | 0.12 |
| 14 | 0.22 | 0.43 | 0.17 |
| 15 | 0.26 | 0.49 | 0.12 |
| Average | 0.24 | 0.41 | 0.12 |
| STD | 0.03 | 0.07 | 0.03 |
| p value | <0.0001 | <0.0001 | — |

As a result from the experimental tests above, it can be concluded that the addition of compound(s) according to b) improve storage stability at higher temperatures. Moreover, the application gets more convenient for the user, because with each application a higher amount of the composition was transferred to the user's hand. This was illustrated by the higher average amount of removed material from the solid composition. This results in higher satisfaction when using such solid compositions.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A solid cosmetic composition for keratin fibers, comprising compounds a) to c):

a) at least one non-silicone lipophilic compound having a melting point greater than 25° C. under atmospheric pressure, b) at least one pulverulent excipient, c) at least one compound selected from the group consisting of a cationic compound and a cationizable compound, wherein a total concentration of water is less than 10% by weight, calculated based on the total weight of the composition, wherein the at least one pulverulent excipient b) is at least one compound selected from the group consisting of a chemically unmodified cellulose, nylon powder, and rice starch, wherein the at least one compound c) is a quaternary ammonium salt surfactant selected from the group consisting of behentrimonium chloride, behentrimonium methosulfate, steartrimonium chloride, soytrimonium chloride, and a combination thereof, wherein a total concentration of the at least one pulverulent excipient b) is from 2% to 12.5% by weight, calculated based on the total weight of the composition, wherein the at least one non-silicone lipophilic compound a) is a $C_{12}$ to $C_{22}$ fatty alcohol selected from the group consisting of cetyl alcohol, stearyl alcohol, cetearyl alcohol, and a mixture thereof; a $C_{12}$ to $C_{22}$ fatty acid monoester of a $C_6$ to $C_{22}$ alcohol selected from the group consisting of myristyl myristate, cocoa butter, shea butter, and a mixture thereof; or a combination thereof, wherein a total concentration of the at least one non-silicone lipophilic compound a) is from 30% to 90% by weight, calculated based on the total weight of the composition, and wherein the composition is a conditioning bar being solid at 25° C. and atmospheric pressure.

2. The composition according to claim 1, wherein the total concentration of the at least one non-silicone lipophilic compound a) is from 50% to 80% by weight, calculated based on the total weight of the composition.

3. The composition according to claim 1, wherein the total concentration of the at least one non-silicone lipophilic compound a) is from 60% to 75% by weight, calculated based on the total weight of the composition.

4. The composition according to claim 1, wherein the total concentration of the at least one pulverulent excipient b) is from 3.5% to 12% by weight, calculated based on the total weight of the composition.

5. The composition according claim 1, wherein the at least one pulverulent excipient b) is the chemically unmodified cellulose and a total concentration of the chemically unmodified cellulose is from 3.5% to 12% by weight, calculated based on the total weight of the composition.

6. The composition according to claim 1, wherein a total concentration of the compound c) is from 0.5% to 10% by weight, calculated based on the total weight of the composition.

7. The composition according to claim 1, wherein a total concentration of the compound c) is from 2% to 6% by weight, calculated based on the total weight of the composition.

8. The composition according to claim 1, further comprising at least one natural oil as a compound d) which is liquid at 25° C. and atmospheric pressure.

9. The composition according to claim 8, wherein the at least one natural oil d) is sweet almond oil, grapeseed oil, sunflower oil, rapeseed oil, olive oil, wheat kernel oil, oat kernel oil, broccoli seed oil, *Camellia sinensis* seed oil, *Cannabis sativa* seed oil, coffee seed oil, hazelnut seed oil, walnut seed oil, castor oil, rice seed oil, or a combination thereof.

10. The composition according to claim 8, wherein a total concentration of the at last one natural oil d) is from 3% to 25% by weight calculated based on the total weight of the composition.

11. The composition according to claim 8, wherein a total concentration of the at last one natural oil d) is from 7.5% to 15% by weight, calculated based on the total weight of the composition.

12. The composition according to claim 1, further comprising at least one non-ionic surfactant as a compound e).

13. A method for conditioning keratin fibers, the method comprising:

i) optionally wetting a hand of a user, ii) rubbing the solid cosmetic composition of claim 1 in the palm of the hand with or without running tap water for a time period of from 5 s to 120 s, thereby transferring the solid cosmetic composition to the hand, and dissolving solid parts, removing solid parts and/or melting solid parts from the composition transferred to the hand, leaving a remaining melted portion of the composition on the hand, iii) putting the solid composition aside and touching the keratin fibers with the hand having the remaining melted portion of the composition on the hand, iv) massaging the composition into the keratin fibers and optionally rinsing-off the composition, v) optionally blow-drying and styling the keratin fibers.

* * * * *